US005474773A

United States Patent [19]

Ward

[11] Patent Number: 5,474,773

[45] Date of Patent: Dec. 12, 1995

[54] HUMAN ROTAVIRUSES, VACCINES AND METHOD

[75] Inventor: Richard L. Ward, Cincinnati, Ohio

[73] Assignee: James N. Gamble Institute of Medical Research, Cincinnati, Ohio

[21] Appl. No.: 114,114

[22] Filed: Aug. 30, 1993

Related U.S. Application Data

[63] Continuation of Ser. No. 614,310, Nov. 16, 1990, abandoned.

[51] Int. Cl.[6] .......................... A61K 39/00; A61K 39/38; A61K 39/15; A61K 39/12; C12N 7/00; C12N 7/04; A01N 63/00; A01N 63/04

[52] U.S. Cl. .................................... 424/184.1; 424/215.1; 424/204.1; 424/93.1; 424/93.6; 435/235.1; 435/236

[58] Field of Search .................................... 424/89, 184.1, 424/204.1, 215.1, 93.1, 93.6; 435/235.1, 236

[56] References Cited

U.S. PATENT DOCUMENTS

| | | | |
|---|---|---|---|
| 4,341,763 | 7/1982 | Zygraich | 424/89 |
| 4,341,870 | 7/1982 | Wyatt et al. | 435/237 |
| 4,571,385 | 2/1986 | Greenberg et al. | 435/172.3 |
| 4,624,850 | 11/1986 | Albert et al. | 424/89 |
| 4,636,385 | 1/1987 | Plotkin et al. | 424/89 |
| 4,751,080 | 6/1988 | Wyatt et al. | 424/89 |
| 4,927,628 | 5/1990 | Chanock et al. | 424/89 |

OTHER PUBLICATIONS

Shaw et al. 1987. Epitope–Specific Immune Responses to Rotavirus Vaccination. Gastroenterology 93:941–50.

Alberts et al. 1987 Isolation and Serotyping of Animal Rotaviruses and Anitgenic . . . 93:123–130.

Tajima, T. et al. (90) Vaccine 8: 70–74.

Ward, R. L et al (1990). J. Virology 64: 3219–3225.

Urasawa, S. et al (1986) J. Gen. Virology 67: 1551–1559.

*Primary Examiner*—Christine M. Nucker
*Assistant Examiner*—Nita M. Minnifield
*Attorney, Agent, or Firm*—Holland & Knight

[57] ABSTRACT

Novel isolated human rotaviruses are disclosed. The novel human rotaviruses in accordance with the instant invention have derived their genomic segments from parental strains of different genogroups and/or serotypes. The novel rotaviruses of the present invention are designated as HRV 248, HRV 456, HRV 89-12C2, HRV 408 and CJN. The human rotavirus designated as HRV 89-12C2, HRV 408, HRV 248 and CJN have been deposited with the American Type Culture Collection (ATCC), 12301 Parklawn Drive, Rockville, Md. 20852, and have been assigned the following ATCC accession nos. VR 2272, VR 2273, VR 2274 and VR 2275, respectively. Also disclosed are novel vaccines formulated with the human rotaviruses of the instant invention, and methods of vaccinating humans against human rotaviruses of multiple serotypes with such vaccines. A novel method for boosting the titers of neutralizing antibodies and expanding the memory of the cells generated which express the neutralizing antibody formed following primary vaccination for preventing rotavirus illnesses induced by human rotaviruses of all serotypes comprising revaccinating the primed subjects with a heterotypic non-human animal rotavirus vaccine, such as with a WC3 bovine vaccine, is also disclosed.

3 Claims, 7 Drawing Sheets

HAV
89-12C2

HUMAN ROTAVIRUSES, VACCINES AND METHOD

This is a continuation of application Ser. No. 07/614,310, filed on Nov. 16, 1990, now abandoned.

FIELD OF THE INVENTION

The present invention relates to isolated human rotaviruses, rotavirus vaccines which stimulate neutralizing antibody to multiple serotypes of human rotavirus, and methods for vaccinating humans against rotavirus illness caused by human rotaviruses of different serotypes and for expanding the titers of pre-existing neutralizing antibodies and memory of the cells producing the antibodies which are formed following primary vaccination against rotavirus disease.

BACKGROUND

Acute, infectious diarrhea is a leading cause of disease and death in many areas of the world. In developing countries, the impact of diarrheal disease is staggering. For Asia, Africa and Latin America, it has been estimated that there are between 3–5 billion cases of diarrhea each year and of those cases, about 5–10 million result in death. Walsh, J. A. et al.: *N. Engl. J. Med.*, 301:967–974 (1979).

Rotaviruses have been recognized as one of the most important causes of severe diarrhea in infants and young children since their discovery in 973. It is estimated that rotavirus disease is responsible for over one million deaths annually. Rotavirus-induced illness most commonly affects children between 6 and 24 months of age, and the peak prevalence of the disease generally occurs during the cooler months in temperate climates, and year-round in tropical areas. Rotaviruses are typically transmitted from person to person by the fecal-oral route with an incubation period of from about 1 to about 3 days. Unlike infection in the 6-month to 24-month age group, neonates are generally asymptomatic or have only mild disease. In contrast to the severe disease normally encountered in young children, most adult rotavirus infections are mild or asymptomatic because such episodes represent reinfection generally as a result of contact with children known to be excreting rotavirus. Offit, P. A. et al.: *Comp. Ther.*, 8(8):21–26 (1982).

Rotaviruses are generally spherical, and their name is derived from their distinctive outer and inner or double-shelled capsid structure. The outer capsid has a diameter of about 70 nm, whereas the inner capsid has a diameter of about 55 nm. Flewett, T. H. et al.: *J. Clin. Path.*, 27:603–614 (1974). Typically, the double-shelled capsid structure of a rotavirus surrounds an inner protein shell or core which contains the genome. The genome of a rotavirus is composed of 11 segments of double-stranded RNA which encode at least 11 distinct viral proteins. Two of these viral proteins designated as VP4 and VP7 are believed to be arranged on the exterior of the double-shelled capsid structure. The inner core of the rotavirus presents one protein, i.e., rotavirus protein designated as VP6. The relative importance of these three particular rotaviral proteins in eliciting the immune response that follows rotavirus infection is not yet clear. Nevertheless, VP6 protein constitutes the group and subgroup antigen, and VP4 and VP7 proteins are the determinates of serotype specificity.

VP7 protein is believed to be a 38,000 MW glycoprotein which is the translational product of genomic segment 7, 8 or 9. This protein is believed to stimulate formation of the major neutralizing antibody following rotavirus infection.

VP4 protein is believed to be a non-glycosylated protein of approximately 88,000 MW which is the translational product of genomic segment 4. This protein is also believed to stimulate neutralizing antibody following rotavirus infection.

Since VP4 and VP7 proteins are the viral proteins against which neutralizing antibodies are directed, they are believed to be prime candidates for development of rotavirus vaccines affording protection against rotavirus illness. However, cells infected with rotavirus do not secrete VP4 and VP7 proteins and, consequently, the immune system is likely to see these proteins only when the cells lyse and the rotaviruses are released.

Human rotaviruses may be divided into six serotypes, i.e., serotypes 1–4 and 8–9, based upon differences in the VP4 and VP7 proteins. Human rotaviruses may also be divided into two subgroups, i.e., subgroups I and II, based on antigenic differences in the inner capsid VP6 protein. Serotype 2 and 8 strains of human rotavirus usually belong to subgroup I, and serotypes 1, 3, 4 and 9 of human rotavirus strains usually belong to subgroup II. Most diseases are presently believed to be caused by rotaviruses belonging to serotypes 1–4 strains and serotype 1 strains have been found to predominate in many geographic regions.

In addition to subgrouping and serotyping, human rotaviruses have been broadly classified into two additional groups, i.e., those with either "short" or "long" RNA patterns based on mobility of their RNA genome segments during gel electrophoresis. Subgroup I human rotavirus strains typically have characteristic "short" electrophoretic patterns whereas subgroup II human rotavirus strains typically have characteristic "long" electrophoretic patterns. The "short" patterns of rotavirus RNA have been associated with an inverse in migration order of gene segments 10 and 11. The majority of rotavirus strains which have been isolated up to now, however, are those with the characteristic "long" patterns.

The human rotaviruses that cause severe diarrhea were originally divided into two "genogroups" based on a genetic linkage between all 11 genomic segments. In 1982, however, a first natural human rotavirus strain in which this linkage appeared to have been broken was isolated. This human rotavirus strain was designated as AU-1. Since that time, a number of human rotaviruses with properties similar to those of the AU-1 human rotavirus strain have been reported in Aboudy, Y. I. et al.: *J. Med. Virol.*, 25:351–359 (1988); Beards, G. M. et al.: *J. Clin. Microbiol.*, 27:2827–2833 (1989); Brown, D. W. G. et al: *J. Clin. Microbiol.*, 26:2410–2414 (1988); Gosh, S. K. et al.: *Arch. Virol.*, 105:119–127 (1989); Sethi, S. K. et al.: *J. Med. Virol.*, 26:249–259 (1988); and Steele, A. D. et al.: *J. Med. Virol.*, 24:321–327 (1988). These human rotaviruses belong to subgroup I, but are identified as serotype 3 and have "long" electrophoretic patterns, properties common to many animal rotavirus strains. Thus, three human rotavirus genogroups have been defined heretofore based on genetic homology of the prototype strains designated as Wa (subgroup II, "long" electropherotype), DS-1 (subgroup I, "short" electropherotype) and AU-1 (subgroup I, "long" electropherotype). See U.S. Pat. Nos. 4,853,333 and 4,341,870 which are believed to be relative to the Wa human rotavirus serotype 1 subgroup II strain.

Because human rotaviruses are formed with segmented genomes, co-infection of cells with two distinct strains of rotavirus can result in the formation of rotavirus progeny having gene segments inherited from both parental strains.

A presumed natural reassortant between subgroup II strains was reported some years ago, but natural reassortants between subgroups I and II human rotaviruses have not as of yet been isolated or identified in Hoshino, Y. et al.: *Proc. Natl. Acad. Sci. USA,* 82:8701–8704 (1985). Recently, however, human rotaviruses having atypical associations between subgroup, serotype and electropherotypes have been reported in Ahmed, M. U. et al.: *J. Clin. Microbiol.,* 27:1678–1681 (1987); Beards, G. M. et al.: *J. Clin. Microbiol.,* 27:2827–2833 (1989); Mascarenhas, J. D. P. et al.: *Virus Res.,* 14:235–240 (1989); Matsuno, S. et al.: *Virus Res.,* 10:167–175 (1988); Steele, A. D. et al.: *J. Med. Virol.,* 24:321–327 (1988). See also U.S. Pat. No. 4,571,385 which apparently discloses a reassortant rotavirus derived from the human rotavirus strain D, serotype 1 and the bovine rotavirus UK strain.

In view of the seriousness of rotavirus illness and that present therapy is limited to non-specific supportive measures, such as replacement of fluids and electrolytes, the development of an effective rotavirus vaccine that offers complete protection against all serotypes of human rotavirus is an important priority for health care in the United States and in developing countries. Several approaches to the development of a rotavirus vaccine have been pursued. Two approaches that have been evaluated in humans include the use of a live, attenuated human rotavirus strain, and the use of a rotavirus strain of animal origin.

Initial rotavirus vaccine studies suggested that bovine rotavirus strains offered partial protection to infants against heterotypic human rotaviruses even in the absence of detectable neutralizing antibody to circulating human strains. See Vesikari, T. et al.: *Lancet,* 2:807–311 (1983); Vesikari, T. et al.: *Lancet,* 1:977–981 (1984); Vesikari, T. et al.: *J. Pediatr.,* 107:189–194 (1985); and Clark, H. F. et al.: *J. Infect. Dis.,* 158:570–587 (1988). Subsequent efficacy trials, however, indicated that these bovine rotavirus vaccines are, at best, only marginally protective. See Hanlon, P. et al.: *Lancet,* 1:1342–1345 (1987); DeMol, P. et al.: *Lancet,* 2:108 (1986); and Lanata, C.G. et al.: *J. Infect. Dis.,* 159:452–459 (1989). For example, the RIT 4237 bovine strain rotavirus (serotype 6) appeared to be successful in preventing clinically significant diarrhea due to rotavirus infection in Finish infants. See Vesikari, T. et al.: *Lancet,* 2:807–811 (1983) and Vesikari, T. et al.: *Lancet,* 1:977–981 (1984). When later evaluated in developing countries, however, it was not as effective. See Hanlon, P. et al.: *Lancet,* 1:1342–1345 (1987); and DeMol, P. et al.: *Lancet,* 108 (1986). See also, U.S. Pat. Nos. 4,636,385; 4,341,763; and 4,190,645.

Rhesus rotavirus (RRV) vaccine strain MMU18006 (serotype 3) has been shown to be immunogenic in several studies, Losonky, G. A. et al.: *Ped. Infect. Dis.,* 5:25–29 (1986); Vesikari, T. et al.: *J. Infect. Dis.,* 153:832–839 (1986); Anderson, E. L. et al.: *J. Infect. Dis.,* 153:823–831 (1986); Gothefors, L. et al.: *J. Infect. Dis.,* 159:753–757 (1989); and Wright, P. F. et al.: *Pediatrics,* 80:473–480 (1987), but has been associated with mild side effects including low grade fever and watery stools. Losonky, G. A. et al.: *Ped. Infect. Dis.,* 5:25–29 (1986); Vesikari, T. et al.: *J. Infect. Dis.,* 153:832–839 (1986); Anderson, E. L. et al.: *J. Infect. Dis.,* 153:823–831 (1986); Gothefors, L. et al.: *J. Infect. Dis.,* 159:753–757 (1989). Clinical evaluations involving RRV vaccine have revealed protection against severe diarrhea in studies conducted in Venezuela, Flores, J. et al.: *Lancet,* 1:882–884 (1987), and Sweden, Gothefors, L. et al.: *J. Infect. Dis.,* 159:753–757 (1989), but no protection in a study of Navajo Indian children. See Santosham, M. et al.: *A Field of Study of the Safety and Efficacy of Two Candidate Rotavirus Vaccines Program and Abstracts: 27th Conference on Antimicrobial Agents and Chemotherapy* (New York), 99 (1987). Thus, efficacy trials with RRV indicated that this vaccine strain protected against homotypic serotype 3 human rotaviruses, but not heterotypic human strains. See Flores, J. et al: *J. Clin. Microbiol.,* 27:512–518 (1989). Moreover, results from other studies conducted involving this rhesus rotavirus vaccine have varied. See Christy, C. et al.: *Pediatr. Res.,* 25:157A (1989). See also U.S. Pat. Nos. 4,751,080 and 4,704,275.

Serotype-specific protection has also been reported after natural rotavirus infection and is correlated with the titer of neutralizing antibody present in the previously infected humans. See Chiba, S. et al: *Lancet,* 2:417–421 (1986). Thus, serotypespecific neutralizing antibody may be the primary determinate of protection against rotavirus disease. Consequently, because there are at least six serotypes of human rotaviruses, a mono-serotype or heterotypic (animal) vaccine may be insufficient to provide complete protection against all serotypes associated with human rotavirus disease.

It has also been reported that primary rotavirus infection in both humans and animals usually result in production of neutralizing antibody to one predominant rotavirus serotype, although some neutralizing antibody to rotaviruses belonging to other serotypes is often detected. See Gerna, G. et al.: Infect. Immun., 43:722–729 (1984); Snodgrass, D. R. et al.: *J. Clin. Microbiol.,* 20:342–346 (1984); Clark, H. F. et al.: *Ped. Infect. Dis.,* 4:626–631 (1985); Puerto, F. I. et al.: *J. Clin. Microbiol.,* 25:960–963 (1987); Zheng, B. J. et al.: *J. Clin. Microbiol.,* 26:1506–1512 (1988); and Brussow, H. et al.: *J. Infect. Dis.,* 158:588–595 (1988). Subsequent rotavirus infection or inoculation with different serotypes has resulted in neutralizing antibody production to the new virus strain and an increase in pre-existing antibody titers to the other rotavirus serotypes involved in previous infection, presumably due to an amnestic response. See Clark, H. F. et al.: *Ped. Infect. Dis.,* 4:626–631 (1985); Kapikan, A. Z. et al.: *J. Infect. Dis.,* 147:95–106 (1983); Urasawa, S. et al.: *Arch. Virol.,* 81:1–12 (1984); Ward, R. L. et al.: *J. Infect. Dis.,* 154:871–880 (1986); Woode, G. N. et al.: *J. Clin. Microbiol.,* 25:1052–1058 (1987); Brussow, H. et al.: *J. Gen. Virol.,* 69:1647–1658 (1988); and Bernstein, D.I. et al.: *Antiviral Res.,* 12:293–300 (1989). These studies have not, however, evaluated the ability of vaccine strains of rotavirus to boost neutralizing antibody titers to heterotypic strains of human rotavirus in infants with pre-existing antibody due to a previous infection. They also have not determined whether previous vaccination with a heterotypic strain can broaden or increase neutralizing antibody responses to human rotaviruses during subsequent natural infection. Notwithstanding, it has been shown that when children are vaccinated with the same rotavirus serotype as the strains causing natural infections, the neutralizing antibody produced after infection prevents "take" of the vaccine at the time of revaccination. See Tajma, T. et al.: *Vaccine,* 8:70–74 (1990).

Consequently, there is a serious need for a rotavirus vaccine which will provide effective immunity against human rotaviruses belonging to at least serotypes 1–4, and in particular serotype 1 which is believed to be the most predominant serotype of human rotavirus.

SUMMARY OF THE INVENTION

In brief, the present invention alleviates certain of the above-mentioned problems and shortcomings in the present state of the rotavirus art through the discovery of novel human rotaviruses. The human rotaviruses of the present invention are generally isolated from fecal material excreted by infants or young children diagnosed with rotavirus illness. Examples of rotavirus strains in accordance with the present invention include HRV 248, HRV 89-12C2 and HRV 408.

The human rotavirus strain designated as HRV 248 is a unique human natural intergenogroup reassortant rotavirus. The HRV 248 strain is neutralized by hyperimmune guinea pig sera to serotypes 2 and 4 of human rotavirus, but is only recognized by serotyping monoclonal antibodies to serotype 4. The HRV 248 strain belongs to subgroup II and has a long electrophoretic RNA pattern based upon mobility of its RNA genome segments upon gel electrophoresis. Hybridization of the RNA of the HRV 248 strain demonstrates that it is a natural human intergenogroup reassortant rotavirus in which its VP4 gene is derived from a serotype 2 human rotavirus and its VP7 gene is derived from a serotype 4 human rotavirus. Seven of the eleven RNA segments of the HRV 248 strain form hybrids with human strains belonging to the prototype Wa human rotavirus strain. The other four RNA segments of the HRV 248 strain hybridize with strains belonging to the prototype DS-1 human rotavirus strain.

The human rotavirus strain designated as HRV 89-12C2 is also a unique human rotavirus which belongs to subgroup II and is serotype 1 as determined by the use of serotyping monoclonal antibodies. The HRV 89-12C2 strain has a long electrophoretic RNA pattern, and hyperimmune guinea pig serum made to this strain neutralizes primarily serotype 1 human rotavirus, but also to a lesser extent, human rotaviruses belonging to serotypes 2–4, 8 and 9.

With respect to the HRV 408 strain, it is neutralized by hyperimmune guinea pig sera to serotypes 1, 2 and 3 of human rotavirus, but is recognized by serotyping monoclonal antibody only to serotype 3. The HRV 408 strain belongs to subgroup II and has the characteristic long electrophoretic RNA pattern typically associated with subgroup II rotaviruses.

The rotavirus strain designated as CJN belongs to subgroup II and has a long electrophoretic RNA pattern according to the mobility of its RNA genome segments in gel electrophoresis. The CJN strain is readily neutralized by hyperimmune guinea pig antisera to serotypes 1, 2 and 4, and hyperimmune antisera to the HRV CJN strain primarily neutralizes serotypes 1 and 3 of human rotavirus. The CJN strain is recognized by only serotyping monoclonal antibody to serotype 1.

The human rotaviruses designated as HRV 89-12C2, HRV 408, HRV 248 and CJN have been deposited with the American Type Culture Collection (ATCC), 12301 Parklawn Drive, Rockville, Md. 20852 under accession nos. VR 2272, VR 2273, VR 2274 and VR 2275, respectively. Although this indicated public availability is the simplest method of obtaining the human rotaviruses of the instant invention, it is not altogether impossible or improbable that similar and functionally substantially identical rotaviruses might be produced by these or other methods in view of the teachings of this invention. Such functionally substantially identical rotaviruses are considered to be biologically equivalent to the human rotaviruses of this invention and therefore are within the general scope of the present invention. Also, such substantially identical rotaviruses, which can be obtained by those skilled in the art by modifying, cultivating, cloning or subcloning the rotaviruses described and thereby provided by the instant invention, without substantially altering the biological and functional properties of the rotaviruses of those cultivated, are within the scope of the present invention. Still further, live, attenuated or inactivated rotaviruses derived from the human rotaviruses of the present invention are also within the general scope of the instant invention.

The human rotaviruses of the present invention when arranged in appropriate combinations are believed to have the unique and surprising ability to stimulate in humans, when administered as vaccines, the formation of neutralizing antibody to multiple serotypes of human rotavirus so that effective protection against subsequent rotavirus illness induced by at least serotypes 1, 2, 3 and 4 and possibly 8 and 9 of human rotavirus is provided. For example, the HRV 248 (VR 2274) strain is believed to have the ability to stimulate neutralizing antibody to at least serotypes 2 and 4 of human rotavirus, whereas the HRV 89-12C2 (VR 2272) strain is believed to possess the capability of stimulating neutralizing antibody to all six human rotavirus serotypes, i.e., 1–4 and 8–9, and in particular to serotype 1. While the HRV 408 (VR 2273) strain is believed to generate neutralizing antibody primarily to serotype 3, it nevertheless is believed that the HRV 408 (VR 2273) strain has the ability to induce neutralizing antibody formation to other serotypes, such as 1 and 2 of human rotavirus. As to the CJN (VR 2275) strain, this strain is believed to be capable of stimulating neutralizing antibody formation to serotypes 1–4 of human rotavirus.

The present invention is further predicated in part upon the discovery of novel vaccines which have the ability to stimulate in humans neutralizing antibody formation to at least serotypes 1–4 of human rotavirus. The novel vaccines of the instant invention may include a single rotavirus or a combination of rotaviruses in admixture with a suitable pharmaceutical carrier for stimulating formation of neutralizing antibody against at least serotypes 1–4 of human rotavirus following vaccination. The rotaviruses selected to form the vaccines of the instant invention may be in the form of live, attenuated strains, or as an alternative, they may be in the form of inactivated strains. When live, attenuated or inactivated strains are selected, the vaccines may be administered orally or intra-nasally. However, it is preferred to administer the live, attenuated strains by the oral or nasal route, and the inactivated strains are preferably administered by parenteral inoculation, such as by intramuscular injection. Examples of vaccines in accordance with the instant invention include the HRV 89-12C2 strain in admixture with a suitable pharmaceutical carrier, or a vaccine comprising the HRV 248 or HRV 408 and HRV 89-12C2 strains in admixture with a suitable pharmaceutical carrier to form vaccines having the ability to elicit neutralizing antibody formation to serotypes 1–4 of human rotavirus following primary vaccination. Other examples include vaccines comprising in admixture with a suitable pharmaceutical vehicle, the combinations of a.) HRV 248, HRV 89-12C2 and HRV 408, b.) HRV 248, HRV 89-12C2, HRV 408 and CJN, c.) HRV 248 and CJN, d.) HRV 248 and HRV 408, or e.) HRV 248, CJN and HRV 408.

The present invention also contemplates the discovery of a novel method for boosting pre-existing neutralizing antibody titers in humans following primary vaccination. This is accomplished in accordance with the instant invention by revaccinating humans with a vaccine containing a rotavirus wherein the genes encoding the VP4 and VP7 proteins are derived from a non-human animal in admixture with a suitable pharmaceutical carrier. It has been surprisingly discovered that the titers of pre-existing neutralizing antibodies induced following primary vaccination may be uniquely increased and memory of the cells that express the neutralizing antibodies may be uniquely expanded by revaccination with such a rotavirus to provide effective protection against subsequent human rotavirus illness caused by any of the human serotypes.

Thus, it is now possible to consistently boost neutralizing antibody titers and expand the memory of the cells which produce such antibodies which are developed after primary immunization by revaccination with the booster vaccines of the instant invention. A typical booster vaccine for revaccination in accordance with the instant invention includes a heterotypic rotavirus strain in the form of, for example, a live naturally-attenuated heterotypic non-human animal rotavirus strain, such as the WC3 bovine rotavirus strain, in admixture with a suitable pharmaceutical carrier. Examples of other heterotypic non-human animal rotavirus strains that may be employed to form the booster vaccines of the instant invention include the NCDV bovine, UK bovine, CP-1 bovine, C3-160 bovine, PP-1 bovine, TC bovine, B223 bovine, KK3 bovine, V1005 bovine, T51 bovine, T67 bovine, T82 bovine, OSU porcine, EE porcine, A-580 procine, G porcine, SB-5 procine and EDIM murine rotaviruses.

In forming the novel vaccines of the instant invention, depending upon the type of vaccine formed, e.g., oral, nasal or parenteral, the pharmaceutical vehicle may be sterile water, normal saline, or the like.

The above features and advantages of the present invention will be better understood with reference to the following accompanying figures, detailed description and example which are illustrative of preferred embodiments of the instant invention.

DESCRIPTION OF THE FIGURES

With reference to the accompanying Figs. which are illustrative of the embodiments within the scope of this invention.

Lane
1 CJN virus (human rotavirus)
2 CJN+rhesus rotavirus (RRV)
3–5 These are all single gene reassortants of CJN and RRV. They all contain only segment 9 of CJN and the other 10 segments are from RRV
6 CJN+rhesus rotavirus (RRV)
7 RRV

Lane
1 Human rotavirus 89-13D1
2 Human rotavirus 89-13D1
3 Human rotavirus 89-13D2
4 Human rotavirus 89-13D2
5 Original stool specimen of 89-12
6 Human rotavirus 89-12C1
7 Human rotavirus 89-12C2
8 Human rotavirus 89-12D1
9 Human rotavirus 89-12D2

Figure 4:
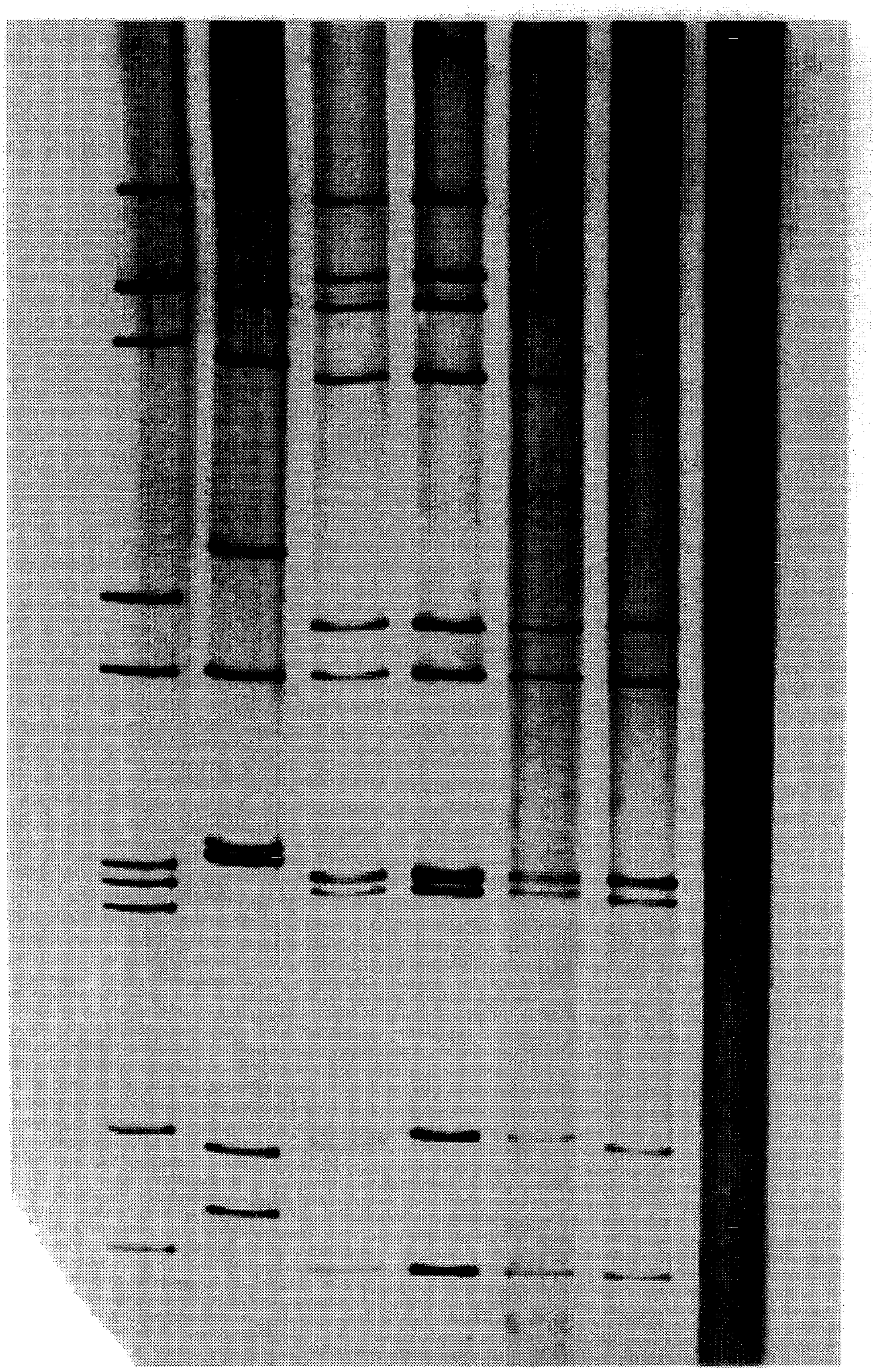

FIG. 4 depicts an electrophoretic analyses of the genomic RNA segments of HRV 408 (ATCC VR 2273) human rotavirus along with other rotavirus strains with long electrophoretic patterns. There are seven lanes in this FIG. 4. From left to right the lanes are designated herein as lanes 1–7 and depict gel electrophorectic patterns for the following rotaviruses:

Lane
1 Human rotavirus strain Wa
2 Murine rotavirus strain Eb
3 Human rotavirus 408 passage 6 (non-plaque purified)
4 Human rotavirus 408 passage 1 after plaque purification
5 Human rotavirus 408 passage 2 after plaque purification
6 Human rotavirus 412 passage 6
7 Human rotavirus 412 from plaque #2

Figure 5A:
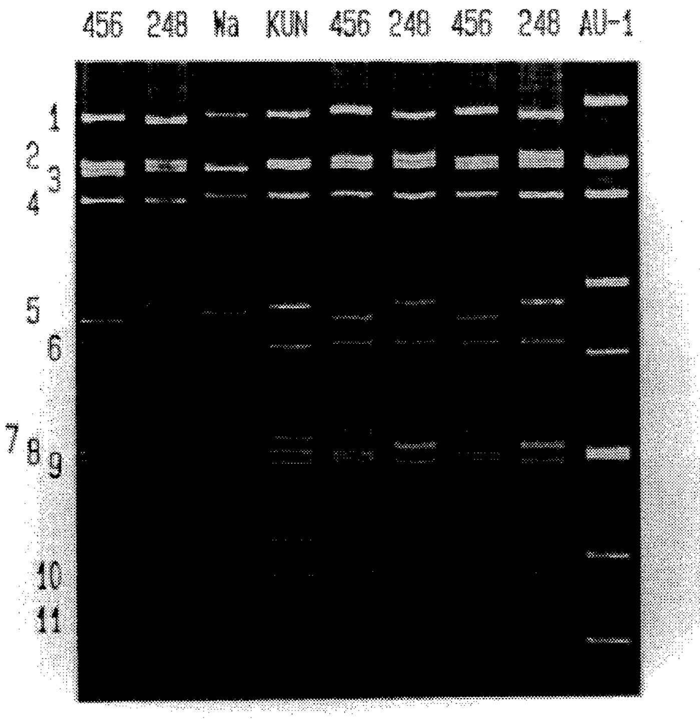
Figure 5B:
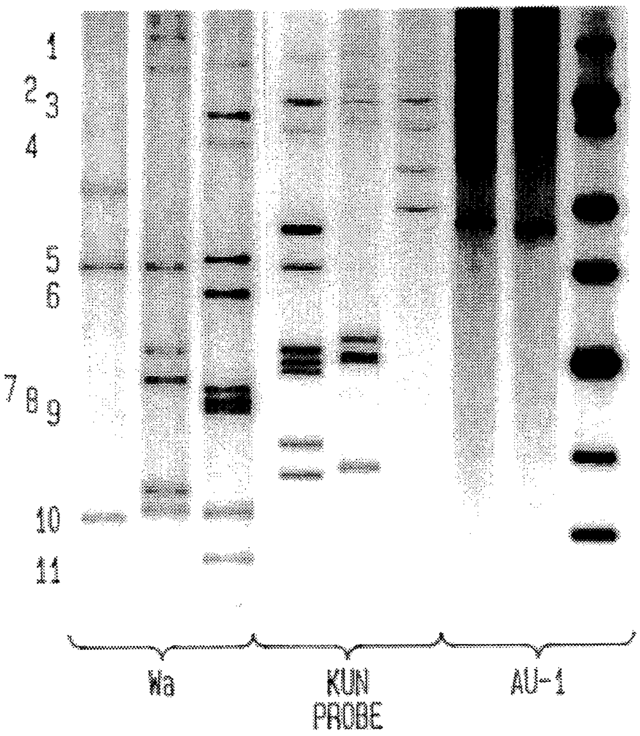

FIGS. 5A–5B depict hybridization patterns obtained between genomic RNAs from HRV 456, HRV 248 (ATCC VR 2274), Wa, KUN, and AU-1 human rotavirus strains and the $^{32}P$-labeled plus stranded RNA probe prepared from Wa, KUN, and AU-1 strains. FIG. 5A depicts a photograph of the ethidium bromide stained gel under UV light illumination. FIG. 5B depicts a photograph of the autoradiogram corresponding to FIG. 5A. Approximate position of the RNA segments of the Wa rotavirus strain is indicated at the left.

Figure 6A:
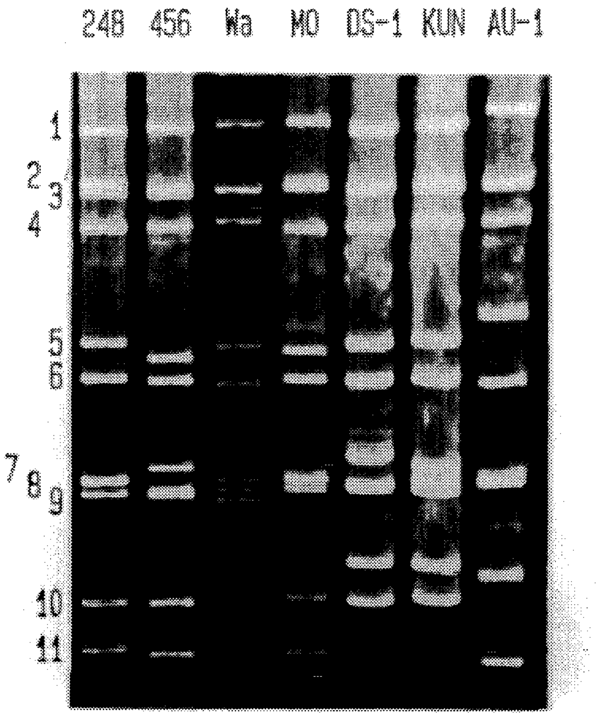
Figure 6B:
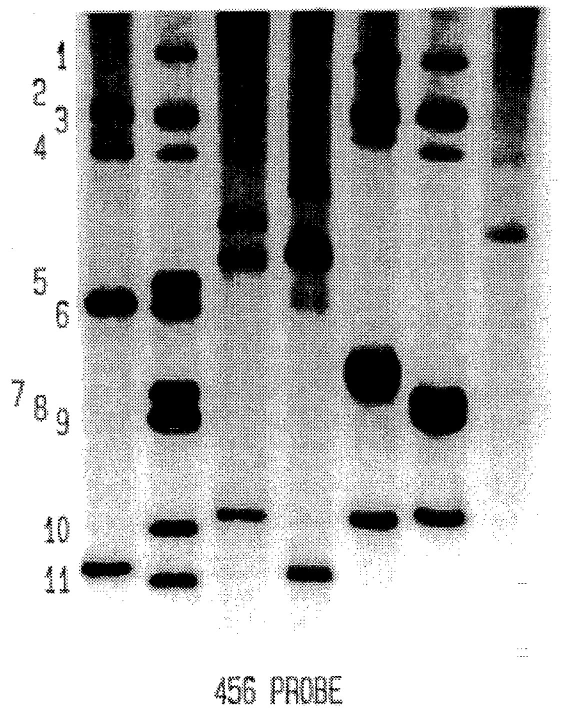

FIGS. 6A–6B depict hybridization patterns obtained between genomic RNAs from human rotavirus strains indicated in FIGS. 6A–6B above in each lane and the $^{32}P$-labeled plus stranded RNA probe prepared from the HRV 456 human rotavirus strain. FIG. 6A depicts a photograph of the ethidium bromide stained gel under UV light illumination. FIG. 6B depicts an autoradiogram corresponding to FIG. 6A. Approximate position of the RNA segments of the HRV 248 (ATCC VR 2274) human rotavirus strain is indicated at the left.

Figure 7A:
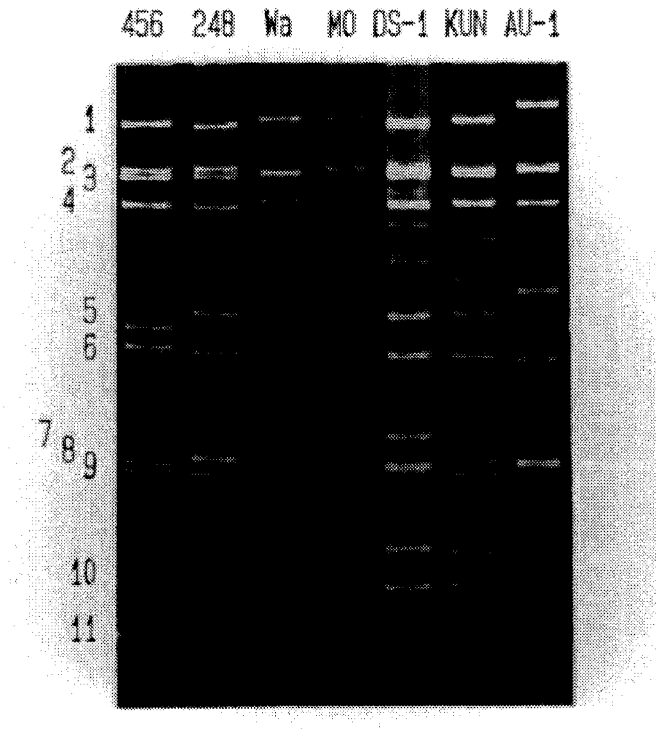
Figure 7B:
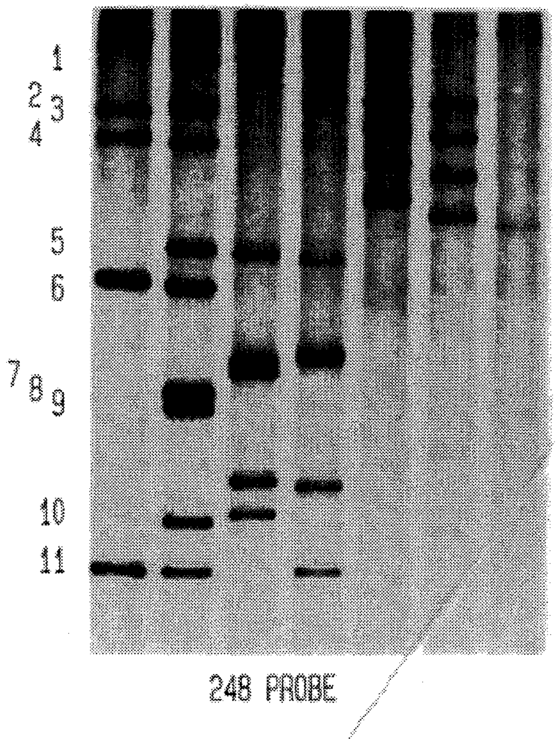

FIGS. 7A–7B depicts hybridization patterns obtained between genomic RNAs from human rotavirus strains indicated in FIGS. 7A–7B in each lane and the $^{32}P$-labeled plus stranded RNA probe prepared from HRV 248 (ATCC VR 2274) human rotavirus strain. FIG. 7A depicts a photograph of the ethidium bromide stained gel under UV light illumination. FIG. 7B depicts an autoradiogram corresponding to FIG. 7A. Approximate position of the RNA segments of the HRV 456 human rotavirus strain is indicated at the left.

DETAILED DESCRIPTION

By way of illustrating and providing a more complete appreciation of the present invention and many of the attendant advantages thereof, the following detailed description is given concerning the human rotaviruses, the rotavirus vaccines which stimulate neutralizing antibody to multiple serotypes of human rotavirus, and methods for vaccinating humans against rotavirus illness caused by rotaviruses of different serotypes and for expanding the titers and memory of the cells that express the pre-existing neutralizing antibodies induced following primary vaccination against rotavirus disease.

Human Rotaviruses

Figure 3:
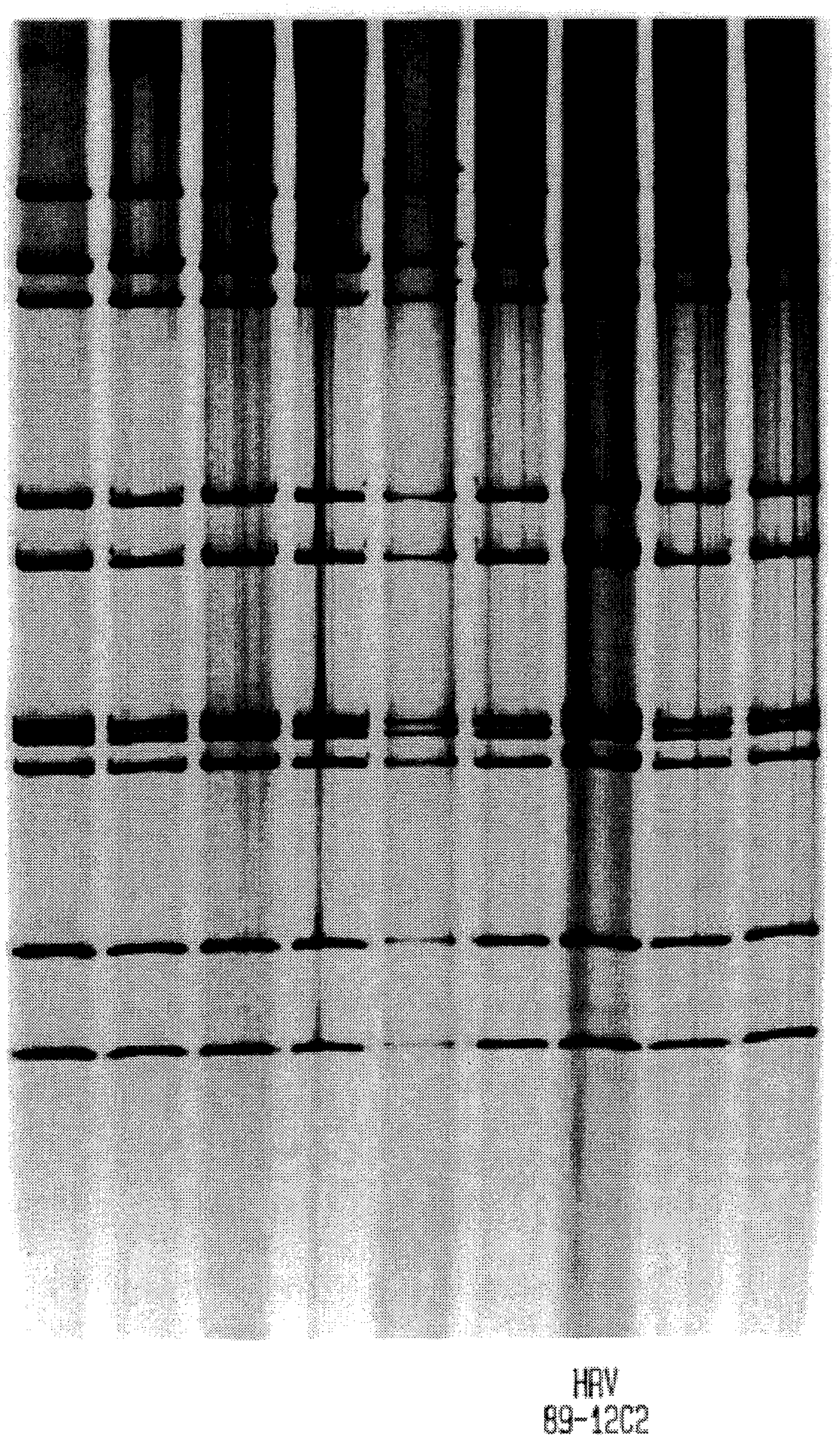
FIG. 3 depicts an electrophoretic analyses of the genomic RNA segments of the HRV 89-12C2 (ATCC VR 2272) human rotavirus along with similar culture adapted strains with long electrophoretic patterns. There are nine lanes in this FIG. 3. From left to right the lanes are designated herein as lanes 1–9 and depict gel electrophoretic patterns for the following rotaviruses.

The HRV 89-12C2 rotavirus was isolated from the stool of a 14-month old subject in Cincinnati, Ohio. The HRV 89-12C2 rotavirus belongs to subgroup II on the basis of gel electrophoresis of its RNA genome, and is serotype 1 on the basis of its reactions to serotyping monoclonal antibodies. In addition to detecting prototype human rotavirus of serotype 1, antiserum to the HRV 89-12C2 rotavirus detects prototype human rotavirus of serotypes 2–4 and 8–9. See Table HRV 89-12C2. The HRV 89-12C2 human rotavirus was cultured-adapted by two passages in primary African green monkey kidney (AGMK) cells and four passages in MA-104 cells, as described in Ward, R. L. et al.: *J. Clin. Microbiol.*, 19:748–753 (1984). It was then plaque purified three times in MA-104 cells and grown two additional passages in these cells. The HRV 89-12C2 human rotavirus strain has been through at least 11 tissue culture passages. One additional passage was made for deposition with the American Type Culture Collection. As indicated hereinabove, the HRV 89-12C2 human rotavirus was deposited with the ATCC and assigned accession no. ATCC VR 2272. The long electrophoretic pattern of the 11th cell culture passage of the HRV 89-12C2 human rotavirus is depicted in FIG. 3. This 11th cell culture passage contained $4\times10^7$ focus forming units/ml, as determined by a fluorescent focus assay, as described in Bernstein, D. I. et al.: *Antiviral Res.*, 12:293–300 (1989). Infants naturally infected with this rotavirus made most neutralizing antibody to serotype 1, but nearly 50% as much to serotype 3 and lower but detectable levels to serotypes 2, 4, 8 and 9 as well. See Ward, R. L. et al.: *J. Infect. Dis., in press, (December* 1990). Vaccination of subjects, who experienced previous natural infections with rotavirus that cause these neutralizing antibody responses, experienced large boosts in neutralizing antibody to all six human rotavirus serotypes.

TABLE HRV 89-12C2

Neutralization Titers of Antiserum to 89-12C2 Against Prototype Human Rotaviruses

| Strain | Serotype | Neutralization Titer |
|---|---|---|
| 89-12C2 | 1 | 256,000 |
| Wa | 1 | 300,000 |
| DS-1 | 2 | 1,000 |
| P | 3 | 5,000 |
| ST-3 | 4 | 1,400 |
| 69M | 8 | 1,000 |
| WI61 | 9 | 3,000 |

Figure 1:
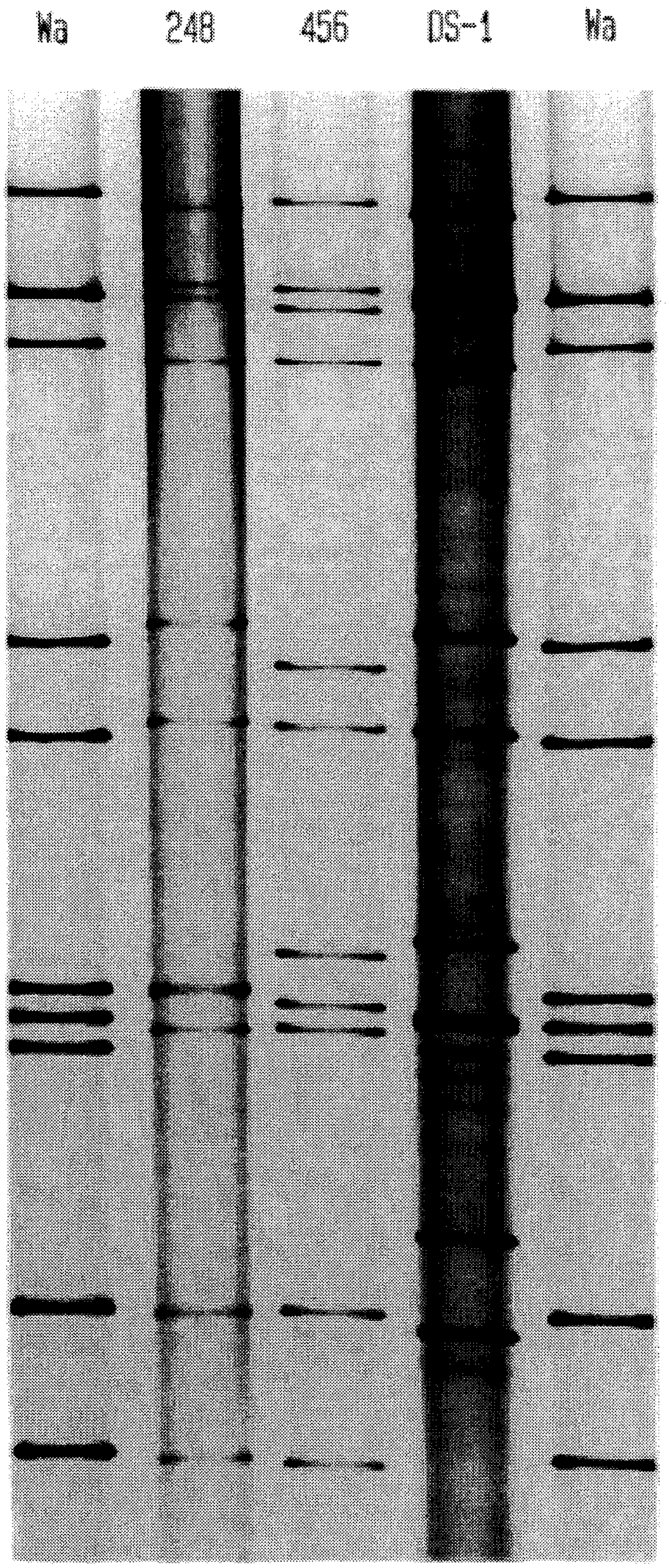
FIG. 1 depicts an electrophoretic analyses of genomic RNA segments of the HRV 248 (ATCC VR 2274) and HRV 456 human rotavirus strains in relation to the prototype Wa and DS-1 human rotavirus strains.

The HRV-248 human intergenogroup reassortant rotavirus was isolated from the stool of an infected 17-month old child in Bangladesh. It was culture adapted as described for the HRV 89-12C2 rotavirus. After two passages in primary AGMK cells and nine passages in MA-104 cells, the HRV-248 human rotavirus was plaque purified three times in MA-104 cells and grown one additional passage in the cells for a total of 15 cell culture passages. Its last titer was $2\times10^7$ focus forming units/ml. An additional passage was made for the preparation sent to the ATCC. As indicated hereinabove, the ATCC assigned the HRV-248 human rotavirus accession no. ATCC VR 2274. Stock cultures were stored in aliquots at −70° C. The long electrophoretic pattern of the genomic RNA of the plaque purified HRV-248 rotavirus is depicted in FIG. 1. The HRV 248 human rotavirus belongs to subgroup II and is primarily neutralized by hyperimmune guinea pig sera to serotypes 2 and 4, but is only recognized by monoclonal antibody to serotype 4. Ward, R. L. et al.: *J. Virol.*, 64:3219–3225 (1990). Further characterization by RNA—RNA hybridization reveals that the HRV 248 human rotavirus is a natural reassortant that derived its VP4 gene from a serotype 2 human rotavirus and its VP7 gene from a serotype 4 human rotavirus. Ward, R. L. et al.: J. Virol., 64:3219–3225 (1990). More particularly, RNA—RNA hybridization shows that the HRV 248 human rotavirus is a natural intergenogroup reassortant which is genetically related to the human rotaviruses belonging to both the Wa and DS-1 genogroups. The HRV 248 strain has formed RNA—RNA hybrids with seven segments of viruses from the Wa genogroup and with four segments of viruses belonging to the DS-1 genogroup. Thus, based on the relative densities of these hybrid bands in autoradiograms, as shown in FIGS. 5–7, the HRV 248 isolate is believed to be a reassortant developed from the Wa and DS-1 genogroups. It is further believed that the HRV 248 human rotavirus will stimulate neutralizing antibody to at least serotypes 2 and 4 of human rotavirus following vaccination.

The HRV 408 human rotavirus was isolated from the stool of a child 9 months of age in Bangladesh. It was culture adapted as described for the HRV 248 (ATCC VR 2274) human rotavirus and after 12 passages was plaque purified four times. The HRV 408 rotavirus has since been passaged two additional times in MA-104 cells. The HRV 408 human rotavirus was deposited with the ATCC and assigned accession no. VR 2273. The HRV 408 human rotavirus belongs to subgroup II on the basis of gel electrophoresis of its RNA genome, and is serotype 3 on the basis of its reactions to serotyping monoclonal antibodies. The HRV 408 human rotavirus nevertheless is neutralized by hyperimmune guinea pig sera to serotypes 1, 2 and 3. The titers of the last passage for the HRV 408 human rotavirus was $3\times10^7$ focus forming units/mi. The long electrophoretic pattern for the RNA genome of the HRV 408 human rotavirus is presented in FIG. 4. While the HRV 408 human rotavirus, when administered as a vaccine, will generate neutralizing antibody primarily to serotype 3, it is believed that it will also generate neutralizing antibody to at least human serotypes 1 and 2.

Figure 2:
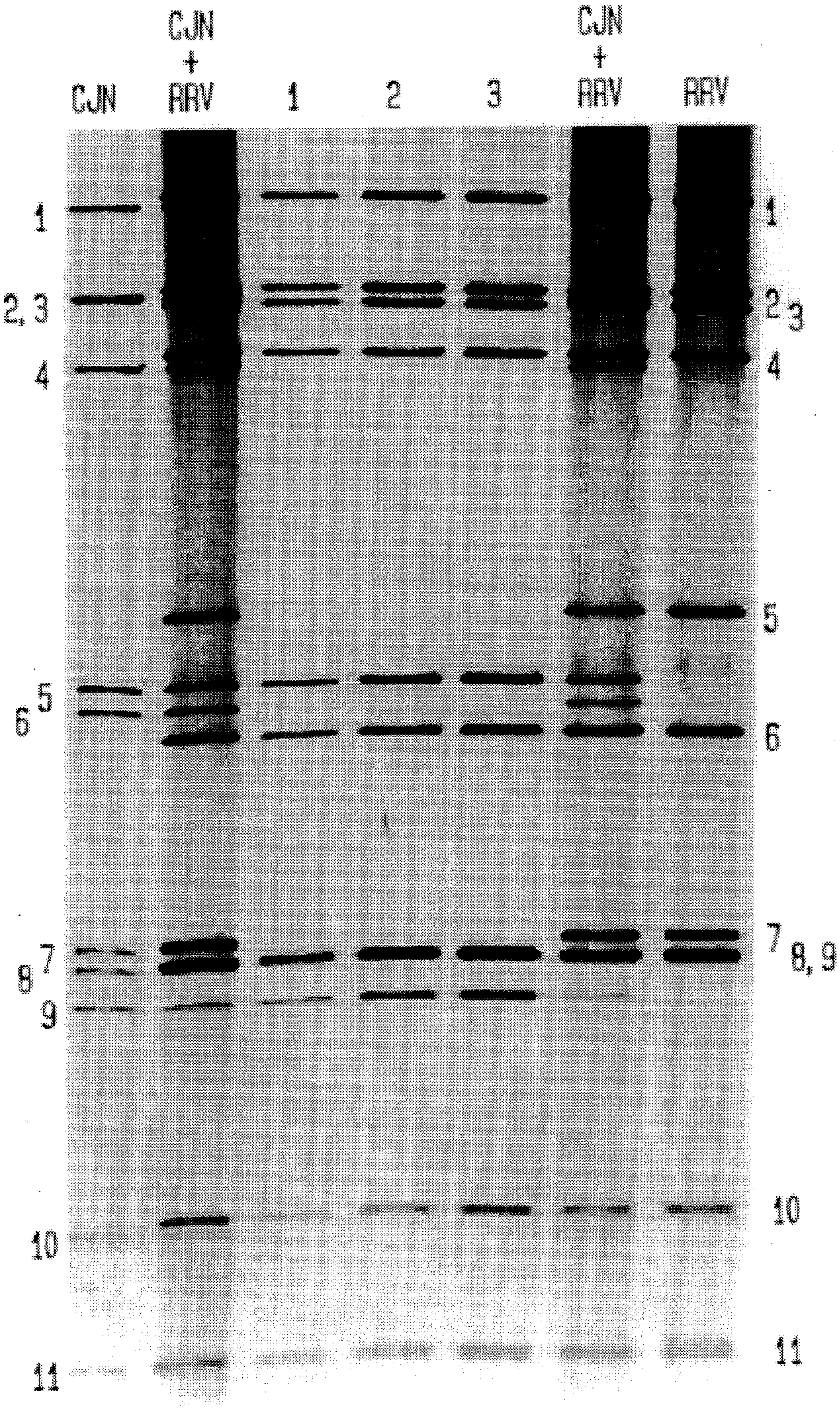
FIG. 2 depicts an electrophoretic analyses of the genomic RNA segments of the CJN (ATCC VR 2275) human rotavirus in relation to the prototype rhesus rotavirus and reassortants between those two strains. There are seven lanes this FIG. 2. From left to right the lanes are designated herein as lanes 1–7 and depict gel electrophoretic patterns for the following rotaviruses.

The CJN human rotavirus was isolated from the stool of an 8-month old child at Children's Hospital Medical Center, Cincinnati, Ohio. It was culture-adapted by two passages in primary AGMK cells and was subsequently passed 4 times, plaque purified 3 times, grown 20 additional passages, plaque purified 3 times and grown 4 additional passages, all in MA-104 cells. Total passages are now 36 and the titer of the last passage is $3\times10^7$ focus forming units/mi. The long electrophoretic pattern of the CJN genomic RNA is depicted in FIG. 2. The CJN human rotavirus has been deposited with the ATCC and assigned accession no. VR 2275. The CJN (ATCC VR 2275) human rotavirus is neutralized by hyperimmune antisera to serotypes 1, 2 and 4, and hyperimmune antisera to CJN neutralized primarily serotypes 1 and 3. Notwithstanding, CJN belongs to subgroup II and is characterized as a serotype 1 human rotavirus. Adults administered unpassaged (unattenuated) CJN had large rises in neutralizing antibody to all four human serotypes tested, i.e., serotypes 1–4 of human rotavirus. It is anticipated that CJN when attenuated or inactivated should stimulate neutralizing antibody to multiple human rotavirus serotypes when given to infants and young children as a primary vaccine.

Electropherotyping of the Human Rotaviral RNA

Polyacrylamide gel electrophoresis of genomic RNA segments extracted from the human rotavirus strains are conducted in accordance with Ward, R. L. et al.: *J. Gen. Virol.*, 69:149–162 (1988).

Subgroup and Serotypic Analyses of Rotaviruses

Subgroup determination of the human rotavirus isolates is made using, for example, subgroupspecific monoclonal antibodies (255/60/125/14 and 631/9/104/56) provided by H. B. Greenberg, Palo Alto, Calif. The analysis may be conducted using an ELISA assay as follows. Wells of microtiter plates are coated with rabbit anti-human rotavirus antibody [1:50 dilution; Dakopatts A/S (Copenhagen)]. After overnight incubation at 4° C., wells are washed and EDTA-treated virus, diluted 1:1 in phosphate buffered saline containing 5% non-fat dry milk (P-NDM), is added and left 1 h at room temperature. Wells are washed and subgroup-specific monoclonal antibodies produced in cell culture and diluted 1:20 in P-NDM are added and left 30 min at room temperature. Wells are again washed and horseradish peroxidase-conjugated rabbit anti-mouse IgG (1:200 in P-NDM; Dakopatts A/S) is added and left 30 min. Finally, wells are washed and incubated 15 min with substrate ($H_2O_2$) and indicator (orthophenylenediamine). The reaction is stopped with 1M $H_2SO_4$ and color development is determined by spectrophotometry.

Serotypic analysis of the human rotaviruses of the instant invention is made using serum of guinea pigs hyperimmunized with purified preparations of, for example, prototype Wa, DS-1, P and ST-3 human rotavirus strains, representative of serotypes 1–4, respectively. Antibody titers to each rotavirus are determined by a focus reduction neutralization assay, such as described in Bernstein, D. I. et al.: *Anti-Viral Research,* 12:293–300 (1989). The lowest dilution (cut-off value) that is used is 1000 for each antisera. Titers are expressed as the reciprocal of the dilution required to reduce the number of focus forming units by 60%.

Preparation of Double-Stranded RNA (dsRNA) For Hybridization Analysis Regarding HRV 248 and HRV 456

Genomic dsRNA is extracted with phenolchloroform from partially purified virions which are prepared from infected MA-104 cells by pelleting at 40,000 rpm for about 1.5 h in a Hitachi RP42 rotor and then by sedimentation through 30% (wt/vol) sucrose at 38,000 rpm for 2 h in a Hitachi RPS40T rotor.

Preparation of Single Stranded RNA (ssRNA) Transcripts Regarding HRV 248 and HRV 456

Single-stranded RNA probes (mRNA) are prepared by in vitro transcription of rotavirus single-shelled particles in 250 ul of 70 mM Trisacetate buffer (pH 8.0) that contain 20 mM magnesium acetate, 100 mM sodium acetate, 8 mM ATP, 0.5 mM GTP, 2.5 mM CTP, 2.5 mM UTP, 0.5 mM S-adenosyl methionine, 0.1% bentonite and [$^{32}$P] GTP (25 uCi per reaction). After 6 h of incubation at 42° C., ssRNAs are purified by phenol-chloroform extraction and lithium chloride precipitation.

RNA—RNA Hybridization Regarding HRV 248 and HRV 456

The $^{32}$P-labeled ssRNA probes from the prototype Wa, KUN, and AU-1 human rotavirus strains are hybridized to the denatured genomic RNAs from the HRV 248 and HRV 456 strains. Likewise, the ssRNA probes prepared from the HRV 248 and HRV 456 human rotavirus strains are hybridized to the denatured genominc RNAs from the prototype Wa (subgroup II, serotype 1), MO (subgroup II, serotype 3), DS-1 (subgroup I, serotype 2), KUN (subgroup I, serotype 2), and AU-1 (subgroup I, serotype 3) human rotavirus strains. Denaturation of dsRNA (approximately 1 ug) is accomplished by 2 min of incubation at about 100° C followed by quenching on ice for 2 min, and to this are added $^{32}$P-labeled probes (10,000 cpm for each denatured dsRNA). Hybridization is allowed to occur at 65° C. for 16 h in a buffer containing 5 mM Tris acetate, 150 mM NaCl, 1 mM EDTA, and 0.1% sodium dodecyl sulfate (pH 7.5). After hybridization, the RNAs are precipitated with ethanol and dissolved in a sample buffer containing 62.5 mM Tris HCl (pH 6.8), 5% (v/v) 2-mercaptoethanol, 10% (v/v) glycerol, 2% (w/v) sodium dodecyl sulfate, and 0.001% (w/v) bromophenol blue. The resulting hybrids, consisting of negative-strand genomic RNA and the positive-strand probe are separated on a 10% polyacrylamide gel with a 4% stacking gel and then are stained with ethidium bromide. Autoradiographs are prepared by exposing dried gels to X-Omat AR films (Eastman Kodak Co., Rochester, N.Y.) at about −80° C.

HRV 248 Rotavirus

As recited hereinbefore, the serotype of the HRV 248 strain are determined by neutralization using antisera to prototype Wa, DS-1, P and ST-3 human rotavirus strains, representative of serotypes 1–4, respectively. Cross-neutralization analyses reveal that these antisera are highly serotype-specific. See Table 1. The HRV 248 strain is neutralized by more than one of these highly serotype-specific antisera as indicated hereinabove.

Based on the "long" electrophoretic patterns of the viral RNA segments from the HRV 248 human rotavirus, as depicted in FIG. 1, it is believed that segment 11 from the isolate is most genetically related to viruses of the Wa genogroup. The subgroups of the HRV 248 virus indicate that segment 6 of the isolate is also most genetically related to the Wa genogroup. See Table 2. Serotypic analyses show that the HRV 248 rotavirus is weakly neutralized by antisera to both DS-1 and ST-3. See Table 2. The segments encoding VP4 and VP7 of the HRV 248 rotavirus are therefore believed to be derived from viruses belonging to separate groups, i.e., the DS-1 and Wa genogroups.

To establish whether the rotavirus isolate HRV 248 has RNA segments that are genetically related to rotaviruses of different genogroups, hybridization studies are performed between RNA segments of this isolate and representatives of the three proposed human rotavirus genogroups. In accomplishing this, genomic dsRNAs from partially purified virions are annealed to $^{32}$P-labeled ssRNA probes of homologous and heterlogous strains. Resulting hybrids are fractioned by polyacrylamide gel electrophoresis and RNA bands are visualized under UV light illumination after staining with ethidium bromide. After drying gels, bands formed with the labeled probes are identified on autoradiograms as depicted in FIGS. 5–7. Homologous RNA—RNA reactions are identified by bands on the autoradiograms that comigrate with genomic dsRNA segments visualized by ethidium bromide staining of the gels; hybrids between genomic segments that are related but not completely homologous form bands that usually do not comigrate with bands that are formed between homologous segments.

Using the $^{32}$P-labeled Wa probe (representative of the Wa genogroup), 7 hybrids are identified with genomic RNAs from HRV 248, as shown in FIG. 5A and 5B. The KUN probe (representative of the DS-1 genogroup) form 4 hybrids with the genomic RNAs from the HRV 248 rotavirus. These results suggest that the 11 gene segments of the HRV 248 strain hybridizes to either the Wa probe or KUN probe, but not both. In contrast, the AU-1 probe shows little homology with genomic RNAs from the HRV 248 rotavirus, although a small amount of hybrid band is observed for 1 or 2 segments. Based upon these results, it is believed that the HRV 248 human rotavirus is an intergenogroup reassortant derived from rotaviruses belonging to two different genogroups, namely the Wa and DS-1 genogroups.

Although exact identification of the origin of gene segments could not be determined for the HRV 248 rotavirus, the relative migration rates of the hybrids provide an indication of the identity of most segments. As revealed in FIGS. 5A–5B, it appears that segments 1, 2, 6, 7, 9, 10 and 11 of HRV 248 rotavirus hybridize with the Wa probe. See Table 3. The remainder of the segments of the HRV 248 rotavirus appear to hybridize with the KUN probe. See Table 3. This proposed origin of gene segments is in agreement with the genetic relationships suggested as a result of electrophoretic, subgroup, and serotypic analysis as shown in FIG. 1 and indicated in Table 2.

The reciprocal hybridization assay, in which a $^{32}P$-labeled ssRNA of the HRV 248 rotavirus is used as a probe, further supports the suggested origin of genome segments for the HRV 248 rotavirus. The HRV 248 probe hybridizes with 7 segments of the Wa and MO strains and 4 segments of the DS-1 and KUN strains, as shown in FIGS. 7A–7B. However, one segment of AU-1 formed a small amount of hybrid with the HRV 248 probe. Thus, this further supports the belief that the HRV 248 human rotavirus is an intergenogroup reassortant derived from the Wa and DS-1 genogroups.

TABLE 1

Homotypic and Heterotypic Neutralizing Antibody Titers of Reference Antisera Used for Serotyping of Rotavirus Isolates

| Antiserum number | Immunizing virus | Serotype | Antisera titers Wa | DS-1 | P | ST-3 |
|---|---|---|---|---|---|---|
| 786 | Wa | 1 | 80,000[a] | 50 | 300 | 300 |
| 293 | DS-1 | 2 | 600 | 40,000 | 800 | 300 |
| 285 | P | 3 | 75 | 50 | 75,000 | 300 |
| 298 | ST-3 | 4 | 300 | 100 | 200 | 400,000 |

[a]Underlined values represent titers to the homologous virus

TABLE 2

Results of Subgroup and Serotypic Analyses For Rotavirus Isolate HRV 248

| Virus Strain | Subgroup | Neutralization titers using reference antisera 786 (Wa) | 293 (DS-1) | 285 (P) | 298 (ST-3) |
|---|---|---|---|---|---|
| HRV 248 | II | 1,000 | 1,200 | <500 | 3,000 |

TABLE 3

Suggested Genogroup of Origin for each of the 11 Segments of HRV 248 Strain

| Virus strain | Genogroup of segment 1 | 2 | 3 | 4 | 5 | 6 | 7 | 8 | 9 | 10 | 11 |
|---|---|---|---|---|---|---|---|---|---|---|---|
| 248 | Wa | Wa | DS-1 | DS-1 | DS-1 | Wa | Wa | DS-1 | Wa | Wa | Wa |

Preparation of Vaccines and Vaccination Methods

Human rotavirus strains of the instant invention that may be used during primary or initial immunization should first be attenuated if administered as live virus vaccines. If an inactivated or subunit vaccine is to be administered by the oral, nasal or parenteral routes, attenuation of course is not necessary.

The following methods may be used to attenuate the primary immunogens. One method for preparation of a vaccine according to the instant invention follows current WHO standards for live poliomyelitis vaccine (oral), with appropriate modifications, as described in Requirements for Poliomyelitis Vaccine (oral), WHO Expert Committee on Biological Standardization, 33rd Report, (Technical Report Series 687) pp. 107–174, WHO:Geneva (1983), which is incorporated herein by reference in its entirety. Another method for preparation of a vaccine involves multiple passages in cell culture in accordance with the standard procedures for attenuation of viral strains for human use, such as disclosed in U.S. Pat. No. 4,636,385, which is also incorporated herein by reference in its entirety. For example, it is reported that 15 passages in cell culture convert a highly virulent porcine rotavirus into an attenuated strain for pigs. Tzipori, S., L. Unicomb, R. Bishop, J. Montenaro, and L. M. Vaelioja: *Archives of Virology*, 109:197–205 (1989). In yet another method that may be used concerns selection of variants that grow at lower temperatures, i.e., variants that are cold-adapted, and which become attenuated. In yet a further method for attenuation of the primary immunogens that may be used is concerned with incorporating the human rotavirus genes encoding the two neutralization proteins, i.e., the viral VP4 and VP7 human proteins, into reassortants that contain at least 1 of the 11 rotavirus gene segments from a heterotypic animal strain. Heterotypic strains that may be used for this purpose include a culture-adapted strain of a mouse rotavirus (EDIM) or a bovine rotavirus, such as WC3. This method may be carried out in accordance with, for example, the procedures disclosed in U.S. Pat. No. 4,571,385, which is incorporated herein by references in its entirety.

Once attenuated or inactivated, the viral preparations of the instant invention will presumably be in a lypholized form. The lyophilized preparation may then be reconstituted with sterile water, normal saline or the like to produce the final vaccine product. A typical live, attenuated vaccine of the present invention may be administered orally or intranasally, the dosage generally being an effective dosage such as on the order of about $1\times10^4$ pfu to about $1\times10^7$ pfu, and preferably about $1\times10^5$ pfu, of live, attenuated rotavirus admixed in, for example, about 1 to 2 mls of a suitable carrier, such as sterile water, normal saline or the like. A typical inactivated vaccine suitable for oral, nasal or parental administration, and preferably intramuscular administration, may comprise about 0.1 micrograms of inactivated rotavirus in admixture with a suitable carrier, such as recited above. The novel vaccinations of the instant invention may be administered in, for example, 1 or 2 ml doses.

While primary or initial vaccination is preferred prior to three months of age, and more preferably soon after birth, primary vaccination may be administered at 6 months to 2 years or more after birth. Of course, it should be appreciated that the longer vaccination is delayed, the more vulnerable infants and young children become to severe rotavirus disease. While the number of strains of rotavirus that are needed in a vaccine is not critical, it is believed that the vaccines of the instant invention when appropriately formulated have the ability to induce neutralizing antibody to at least serotypes 1–4 of human rotavirus, and more particularly to serotypes 1–4 and 8–9, which should be sufficient to confer protection against severe disease caused by infecting human rotavirus strains of all serotypes subsequent to vaccination.

Each combination of rotavirus strains of the instant invention is believed to possess the ability to stimulate cross-neutralizing antibody to at least serotypes 1–4 and possibly to serotypes 1–4 and 8–9 of human rotavirus when administered to humans as a vaccine. For example, it is shown that following natural infection with HRV 89-12C2 or CJN, titers to serotypes 1–4 are produced. In the event that titers to, for example, serotypes 2 and 4 are low, the primary vaccines may be formulated with, for example, the combination of HRV 248 and HRV 89-12C2 and/or CJN. It is also possible that culture-adaptation and plaque purification may select a variant of one of the rotaviruses of the instant invention that stimulates little neutralizing antibody to a particular serotype. For example, in the event that the HRV 89-12C2 when administered as a vaccine stimulates little neutralizing antibody to serotype 3, the inclusion of HRV 408 in the vaccine should augment the titer to this serotype. It should therefore be appreciated that any combination of the disclosed human rotaviruses may be employed to formulate vaccines to elicit neutralizing antibody to at least serotypes 1–4 of human rotavirus.

Revaccination with Heterotypic Animal Vaccines For Boosting Neutralizing Antibodies Induced Following Vaccination As already indicated above, the present invention contemplates a novel method for increasing the titers of and expanding the memory of the cells which express pre-existing neutralizing antibodies formed following vaccination against rotavirus disease. Generally speaking, the method contemplates boosting neutralizing antibody titers developed after primary immunization with a rotavirus wherein its VP4 and VP7 genes are derived from non-human animal rotaviruses. More particularly, this can be accomplished by revaccinating humans with a heterotypic non-human animal rotavirus vaccine within preferably about two to about four months following primary vaccination with a human rotavirus vaccine. While the booster immunization is preferably administered in the form of an oral or nasal live, attentuated heterotypic animal virus preparation, such as a WC3 bovine rotavirus vaccine, the booster vaccine may also be administered in the form of an inactivated rotavirus vaccine or by parental inoculation of an inactivated vaccine. Examples of other heterotypic non-human animal rotaviruses that may be used to formulate the booster vaccines of the instant invention include NCDV bovine, CP-1 bovine, C3-bovine, PP-bovine, TC bovine, B223 bovine, KK3 bovine, V1005 bovine, T51 bovine, T67 bovine, T82 bovine, OSU porcine, EE porcine, A-580 porcine, G porcine, SB-5 porcine, UK bovine, EDIM murine rotaviruses and the like. An example of a booster vaccine that may be employed in accordance with this invention may be prepared and administered in dosage amounts in accordance with the teachings herein or in accordance with Bernstein, et al.: *J. Infect. Dis.*, 162:1055–1062 (1990); Clark, H. F., et al.: *Am. J. Dis. Child,* 140:350–356 (1986); and U.S. Pat. No. 4,636,385, all of which are incorporated herein by reference in their entireties.

This unique method of the instant invention is predicated in part upon the present realization that, as with other vaccines, immunity to rotavirus may need to be boosted sometime after primary immunization. It is also predicated in part upon the present belief that a second natural rotavirus infection with the same serotype may be partially inhibited, as reported by Tajima, T., et al.: *Vaccine,* 8:70–74 (1990), probably due to serotype-specific neutralizing antibody developed after the first natural infection. This novel method of the instant invention is also predicated upon the discovery that a previous natural infection with a serotype 1 human rotavirus strain prior to vaccination with a WC3 bovine vaccine does not inhibit reinfection with the heterotypic WC3 bovine strain, as reported by Bernstein, et al.: *J. Infect. Dis.,* 162:1055–1062 (1990). See Tables 5, 6 and 8. Still further, these unique methods of the instant invention are also based upon the discovery that vaccines like WC3 bovine stimulate cross-reactive neutralizing antibody to multiple human rotavirus serotypes in infants naturally infected with serotype 1 infection before vaccination, as reported in Ward, et al.: *J. Infect. Dis.,* 162:1298–1303 (December 1990). See also Tables 5–8.

It has been further discovered that although vaccination with a WC3 bovine vaccine does not induce neutralizing antibody to human rotavirus strains when it is the primary immunogen, it surprisingly causes large and nearly equivalent (on the average: 12 fold) rises in neutralizing antibody to human serotypes 1–4 when it is the boosting immunogen. See Tables 4–8. In fact, it was surprisingly discovered that the final neutralizing antibody titers to human serotypes are nearly as great as when subjects have sequential natural infections with serotype 1 rotaviruses. See Tables 4–8. These results indicate that although the WC3 bovine strain and the natural human rotavirus strains are distinct serotypes, epitopes on these strains are sufficiently similar for revaccination with WC3 bovine strain to boost neutralizing antibody titers to human serotypes in subjects already primed with primary human rotavirus vaccines and to expand the memory of cells that express such antibodies for effective neutralization of human rotaviruses of all serotypes.

Thus, it is believed that the instant invention now makes it possible to consistently boost titers and expand the memory of the cells that express the neutralizing antibody developed after primary immunization by revaccination with a heterotypic animal rotavirus strain. In other words, the titers and memory of the cells that produce the pre-existing neutralizing antibody induced by primary human rotavirus vaccination can be boosted or expanded to afford protection against subsequent illnesses caused by human rotavirus of all serotypes by practicing the methods of the instant invention.

The present invention relative to the boosting of the titers and memory of the cells that produce pre-existing neutralizing antibodies induced with primary vaccination by revaccinating with a heterotypic non-human animal rotavirus will now be better illustrated with reference to the following example.

EXAMPLE

Virus Strains

The passage history that is used to culture adapt and prepare the WC3 bovine rotavirus (serotype 6) vaccine has been previously described by Clark, H. F. et al.: *Am. J. Dis. Child,* 140:350–356 (1986). The WC3 stock used for laboratory investigations is grown in MA-104 cells after direct inoculation with the vaccine preparation. Aliquots of this stock virus are stored at −70° C. Human rotaviruses that are used in this study are prototype strains Wa, DS-1, P and ST-3, representatives of serotypes 1–4, respectively.

Study Plan

Briefly, healthy infants 2 to 12 months of age are administered placebo (103 subjects) or vaccine (103 subjects). Subjects are followed during the subsequent "rotavirus season" to determine the immunogenicity, reactogenicity and efficacy of the vaccine. Blood specimens (0.5 ml) are collected at the time of vaccination, 25 to 31 days after vaccination, and in near the end of the rotavirus season. These are used for rotavirus antibody measurements. Stools are collected at the times of diarrheal illness and analyzed for rotavirus antigen by ELISA to detect symptomatic rotavirus infections. Rotaviruses detected in this manner are characterized to determine their electropherotype (electrophoretic analysis of viral RNAs) and serotype (ELISA using monoclonal antibodies specific for VP7). Asymptomatic infections are detected by rises in serum rotavirus IgA and IgG and are confirmed by rises in serum neutralizing antibody titers to the serotype 1 Wa strain.

Analysis of Rotavirus Antibody In Serum Specimens

Serotype-specific neutralizing antibody is determined by a focus reduction neutralization assay which has been described in detail in Bernstein, D. I. et al.: *Antiviral Res.*, 12:293–300 (1989).

Statistical Analyses

Comparisons of geometric mean titers (GMT) is performed by using a two-tailed Student's t test except where noted.

Serotype-Specific Antibody Titers Following Natural Symptomatic Rotavirus Infection: Effect of Previous WC3 Vaccination Forty-six of 206 infants that are enrolled in the WC3 bovine vaccine trial experience symptomatic rotavirus infection during the observation period. These include 25/103 placebos and 21/103 vaccinees, all of whom developed WC3 bovine neutralizing antibody following vaccination. None of these 46 subjects have been infected with rotavirus prior to the time of enrollment, as is determined by the absence of serum rotavirus IgA.

Serum specimens are collected from these symptomatically-infected subjects at the end of the rotavirus season and are examined to determine the effect of previous WC3 bovine vaccination on serotype-specific antibody titers. Sera from 29 subjects are randomly-selected for analysis, including specimens from 15/25 infected placebo recipients and 14/21 infected vaccinees. The human rotavirus strains that infect these 29 subjects are all identified as serotype 1 by ELISA. In addition, the 21 isolates that are examined all have similar electropherotypes. Thus, these infections are apparently due to very similar strains of human rotavirus.

Each of the 29 sera that are examined have the highest titer of neutralizing antibody to the serotype 1 Wa strain (Table 4). These subjects, however, also make substantial amounts of neutralizing antibody to the serotype 3 strain (P) but lesser quantities to the serotypes 2 (DS-1) and 4 (ST-3) strains. Thus, the infecting serotype 1 strains causes antibody rises to heterotypic human rotaviruses during primary infection. Furthermore, the GMT to the Wa strain is essentially identical in vaccinees and placebo recipients. Because none of the symptomatically-infected vaccinees have detectable (20) neutralizing antibody to the Wa strain following vaccination, this result is not unexpected. Although the GMT to the DS-1 strain is significantly greater in vaccinees than placebo recipients ($p=0.009$), these titers are still much smaller than the GMT to Wa. The GMTs to ST-3 and P strains are not significantly (p 0.05) different between placebo recipients and vaccinees. Thus, previous vaccination with WC3 has no detectable effect on neutralizing antibody titers to Wa, a serotype 1 strain, following a subsequent symptomatic infection with a serotype 1 rotavirus and only a small effect on neutralizing antibody titer to one of the three strains belonging to the heterotypic human rotavirus serotypes that are tested.

Changes in neutralizing antibody to WC3 following a subsequent natural rotavirus infection are also examined. Sera from 7 randomly-selected vaccinees who experience a subsequent infection with a serotype 1 rotavirus show significant ($p=0.02$) increases in neutralizing antibody titers to WC3 (Table 5) although the resulting titers for these 7 subjects are significantly ($p=0.003$) less than to the serotype 1 Wa strain (GMT=1309; range =240–5100). Sera from 7 vaccinated subjects who do not experience a subsequent natural rotavirus infection (selected from those with high titers to WC3 bovine to allow decreases in titers to be quantified) have significant ($p=0.003$) decreases in neutralizing antibody to WC3 during this period. Seven randomly-selected placebo recipients that are infected with human rotavirus make no detectable (20) neutralizing antibody to WC3. Thus, previous vaccination with WC3 results in an anamnestic antibody response to this virus during a subsequent natural serotype 1 rotavirus infection.

Serotype-Specific Antibody Titers Following Natural Asymptomatic Rotavirus Infection: Effect of Previous WC3 Vaccination Asymptomatic natural rotavirus infections are also detected during the WC3 vaccine study as determined by rises in serum rotavirus IgA and IgG and confirmed by rises in neutralizing antibody to the Wa strain. These occur in 29 subjects including 16 placebo recipients and 13 vaccinees. Thirteen of each group are selected to determine the effect of previous WC3 bovine infection on serotype-specific antibody titers. Because 3 of the placebo recipients experience a previous natural infection (2 with serotype 1 strains and 1 with a serotype 3 strain based on relative neutralizing antibody titers to serotypes 1–4), the effect of natural infection on serotype-specific antibody titers following a subsequent natural reinfection can also be examined in this small number of subjects.

All but one of the 26 asymptomatically infected subjects that are examined develop the highest antibody titer to the Wa strain regardless of whether they are previously infected with WC3 or a natural serotype 1 strain, or have not been previously infected (Table 6). The one exception is the subject previously infected with the serotype 3 strain who, upon being reinfected with a presumed serotype 1 strain, develops the highest titer to serotype 3. The relative amounts of neutralizing antibody to serotypes 1–4 in all but this one subject are very similar to those found in symptomatically infected subjects (see Table 4). Even the slight but significant (p=0.001) increase in antibody to DS-1 in vaccinees relative to placebo recipients is again observed. In this case, however, a slight but significant increase (p=0.005) in antibody to ST-3 is also observed in the vaccinees relative to placebo recipients. These results indicate that the same or very similar strains of rotavirus cause natural symptomatic and asymptomatic infections during the study period.

The actual titers of neutralizing antibody that are developed to the serotype 1 Wa strain are nearly identical in asymptomatically-infected vaccinees and placebo recipients who have not experienced previous natural infections (Table 6), an observation which also has been made with symptomatically infected subjects (see Table 4). These titers are, however, significantly less (p=0.03; one-tailed Student's t test) than observed in subjects with symptomatic infections. Thus, the magnitude of the immune response following a natural serotype 1 rotavirus infection appears to be related to the symptom scores.

Although previous vaccination with WC3 has little effect on the magnitude of neutralizing antibody to human strains following a subsequent natural rotavirus infection, a previous natural infection appears to have a large effect on neutralizing antibody titers following a subsequent natural infection. The 3 subjects who have sequential natural infection have final GMTs to the four rotavirus serotypes tested that average 7-fold greater than placebo or vaccine recipients following single natural infections. In addition, the average increase in GMT for the four serotypes is 25-fold between the first and second infections.

Serotype-Specific Antibody Titers Following WC3 Vaccination: Effect of a Previous Natural Infection Twenty-five infants in the WC3 vaccine trial, all between 7 and 12 months of age at the time of enrollment, have already experienced a natural rotavirus infection based on the presence of serum rotavirus IgA and neutralizing antibody to human strains in sera which is obtained prior to vaccination. Twenty-four of these, including 16 placebo recipients and 8 vaccinees, are infected with a serotype 1 strain as determined by their relative neutralizing antibody titers to strains representative of serotypes 1 through 4 (Table 7). All 24 have similar ratios of neutralizing antibody to the 4 human serotypes and these ratios are very similar to those of placebo recipients who have become naturally infected during the observation period following vaccination (see Table 4). It is, therefore, believed that the serotype 1 strains that cause these infections over two "rotavirus seasons" are antigenically similar.

Seven of the 8 previously infected vaccinees seroconvert to WC3 when administered vaccine as compared to 93 out of 95 subjects who have not been previously infected (p=0.20). Furthermore, antibody titers to WC3 in subjects who seroconvert following vaccination are not significantly different (p=0.18) between the 7 previously infected vaccinees (GMT=75) and the 93 vaccinees who have not been previously infected (GMT=106). Thus, a previous natural rotavirus infection does not inhibit reinfection with WC3 bovine nor affect antibody responses to this heterologous virus.

Following WC3 vaccination, the 7 previously infected subjects who seroconvert to WC3 have large and nearly equivalent (9.7–13.7) fold rises in neutralizing antibody titer to human rotaviruses belonging to serotypes 1–4 (Table 8). Even subjects with titers below the limit of detection (i.e. 20) to serotypes 2 or 4 prior to vaccination have large rises to these serotypes. The average magnitude of these rises (12-fold) is approximately one-half as large as is observed in the 3 subjects who experience sequential natural infections. The final GMT to the 4 human rotavirus strains in these 7 subjects after vaccination is significantly greater than to WC3 bovine (minimum difference =WC3 vs. DS-1; p=0.05 as determined by a one-tailed Student's t test). As reported in D. I. Bernstein et al., J. Inf. Dis., 162:1055–1062 (1990), only 2 out of 93 previously uninfected subjects who seroconvert to WC3 bovine following vaccination develop antibody rises to human strains. Thus, previous infection with serotype 1 rotavirus strains prime these subjects such that following reinfection with the heterologous WC3 bovine strain, antibody titers to all four human serotypes are consistently and dramatically boosted.

TABLE 4

Neutralizing Antibody Titers to Human Rotavirus in WC3 Vaccinees or Placebo Recipients Following a Subsequent Symptomatic Serotype 1 Rotavirus Infection

| Subjects | No. of subjects tested | GMT to human rotaviruses Wa (1)* | DS-1 (2) | P (3) | ST-3 (4) |
|---|---|---|---|---|---|
| Vaccinees | 14 | 1033 (100)+ (300–5100)§ | 88° (19) (<20=–480) | 288 (28) (80–640) | 128 (12) (35–1000) |
| Placebo recipients | 15 | 1025 (100) (280–4260) | 25 (2) (<20–75) | 459 (45) (190–1700) | 78 (8) (30–300) |

*Serotypes
+Percentage GMT relative to Wa
° Significantly greater (p = .009) than placebo recipients
§Range of titers
=Values of <20 considered as 10 for calculations

TABLE 5

Neutralizing Antibody Titers to WC3 in Vaccinees or Placebo Recipients Before and After A Subsequent Serotype 1 Rotavirus Infection

| Subjects | No. of subjects tested | GMT to WC3 Before natural infection* | After natural infection+ |
|---|---|---|---|
| Vaccinees who experience a subsequent natural infection | 7 | 51 (20–120)= | 227§ (40–1150) |
| Placebos who experience a natural infection | 7 | N.D. | <20 (<20) |
| Vaccinees who do not experience a subsequent natural infection | 7 | 268 (160–600) | 115§ (50–220) |

*Before: 25–31 days after vaccination (October-December, 1988)
+After: June, 1989
=Range of titers
§Significantly different (p < .02) between 25–31 days after vaccination and near the end of the rotavirus season
N.D. Not determined

TABLE 6

Neutralizing Antibody Titers to Human Rotaviruses in WC3 Vaccinees or Placebo Recipients Following a Subsequent Asymptomatic Serotype 1 Rotavirus Infection

| Subjects | No. of subjects tested | GMT to human rotaviruses Wa (1)* | DS-1 (2) | P (3) | ST-3 (4) |
|---|---|---|---|---|---|
| Vaccinees | 13 | 682 (100)+ (60–5120)§ | 142 (21)= (<20°–540) | 239 (35) (<20–3500) | 73= (11)= (<20–295) |
| Placebo recipients | | | | | |
| Not previously infected before enrollment | 10 | 602 (100) (60–1200) | 31 (5) (<20–140) | 275 (46) (35–840) | 19 (3) (<20–56) |
| Previously infected with serotype 1 strain before enrollment | 2 | 4820 (100) (3400–6800) | 188 (4) (110–320) | 1930 (40) (960–3850) | 400 (8) (320–500) |
| Previously infected with serotype 3 strain before enrollment | 1 | 7700 (100) | 640 (8) | 15000 (195) | 300 (4) |

*Serotype
+Percentage GMT relative to Wa
=Significantly greater (p ≦ .005) than previously uninfected placebo recipients
§Range of titers
°Values of <20 considered as 10 for calculations

TABLE 7

Neutralizing Antibody Titers to Human Rotaviruses at the Time of WC3 Vaccination in 24 Infants Previously Infected with Serotype 1 Rotaviruses
GMT to human rotaviruses

| Wa (1)* | DS-1 (2) | P (3) | ST-3 (4) |
|---|---|---|---|
| 414 (100)+ (35–2240)= | 17 (4) (<20§–95) | 184 (44) (<20–1200) | 34 (8) (<20–215) |

*Serotype
+Percentage GMT relative to Wa
=Range of titers
§Values of <20 considered as 10 for calculations

TABLE 8

Changes in Neutralizing Antibody Titers to WC3 and Human Rotavirus Serotypes 1–4 Resulting from WC3 Infection in Seven Vaccinees with Previous Serotype 1 Infections
GMT to rotavirus strains

| WC3 (6)* Pre | Post | Wa (1) Pre | Post | DS-1 (2) Pre | Post | P (3) Pre | Post | ST-3 (4) Pre | Post |
|---|---|---|---|---|---|---|---|---|---|
| <10 | 75 | 199 | 1939 | 11 | 144 | 85 | 978 | 20 | 273 |
| (>7.5)+ | | (9.7) | | (13.1) | | (11.5) | | (13.7) | |

*Serotypes
+Fold-rises in GMT

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described my invention, I claim:

1. A vaccine for providing immunological protection against rotavirus illness in humans, said vaccine comprising:

a live attenuated human rotavirus strain in admixture with a suitable pharmaceutical carrier, said live attenuated human rotavirus strain being serotype 1, subgroup II and designated as HRV 89-12C2. ATCC No. VR 2272, said live attenuated human rotavirus strain having the ability to stimulate formation of neutralizing antibody against human rotavirus serotypes 1–4 and 8–9 and to confer protection against human rotavirus infection, said live attenuated human rotavirus strain further having gene segments which encode for human rotavirus VP4 and VP7 proteins, respectively.

2. An isolated rotavirus strain designated as HRV 89-12C2 and deposited with the ATCC under accession no. ATCC VR 2272.

3. A method for providing immunological protection against rotavirus illness in humans, said method comprising administering to the human the vaccine as recited in claim 1.

* * * * *

UNITED STATES PATENT AND TRADEMARK OFFICE
Certificate

Patent No. 5,474,773 Patented: December 12, 1995

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Richard L. Ward, Cincinnati, Ohio; and David I. Bernstein, Loveland, Ohio.

Signed and Sealed this Eighteenth Day of February 2003.

LYNETTE R. F. SMITH
*Supervisory Patent Examiner*
Art Unit 1645